United States Patent [19]

Ury

[11] 4,287,752
[45] Sep. 8, 1981

[54] APPARATUS AND METHOD FOR ANALYZING THE HYDROCARBON TYPE COMPOSITION OF GASOLINE

[75] Inventor: George B. Ury, Naperville, Ill.

[73] Assignee: Standard Oil Co. (Indiana), Chicago, Ill.

[21] Appl. No.: 63,427

[22] Filed: Aug. 3, 1979

[51] Int. Cl.³ .............................................. G01N 31/06
[52] U.S. Cl. ........................................ 73/23.1; 55/67
[58] Field of Search ..................... 73/23.1; 55/67, 197, 55/386

[56] References Cited

U.S. PATENT DOCUMENTS

| | | | |
|---|---|---|---|
| 3,068,686 | 12/1962 | Harmon | 73/23.1 |
| 3,112,639 | 12/1963 | Maxwell | 73/23.1 |
| 3,225,520 | 12/1965 | Burow | 73/23.1 X |
| 3,234,779 | 2/1966 | Dawson | 73/23.1 |

OTHER PUBLICATIONS

"Physico-Chemical and Gas Solid Chromatographic Evaluation of Surface-Modified Silica Gels", by Datar et al. from J. of Chromatography, 114 (1975), 29-38.

*Primary Examiner*—James J. Gill

*Attorney, Agent, or Firm*—Lansing M. Hinrichs; William T. McClain; William H. Magidson

[57] ABSTRACT

Disclosed is a method and an apparatus for analyzing the composition of a gasoline-range petroleum product using a new copper on silica gel adsorption composition. The copper on silica gel adsorption composition is capable of separating olefins from saturates in a mixture by temporarily retaining the olefins while allowing the saturates to pass through. The method of analysis entails passing a gasoline sample through an absorption column whereby the aromatics are retarded while the saturates and olefins pass through. The saturates and olefins are then directed through the copper on silica gel composition wherein the olefins are retained while the saturates pass through into a detector and are measured. Once all the saturates are removed from the system, the aromatics are backflushed from the absorption column and are routed into the detector for measurement. Lastly, the copper on silica gel composition is elevated in temperature so as to release the olefins which then likewise pass into the detector for measurement. The flow of the various streams is facilitated by a compatible carrier gas, such as nitrogen.

12 Claims, 5 Drawing Figures

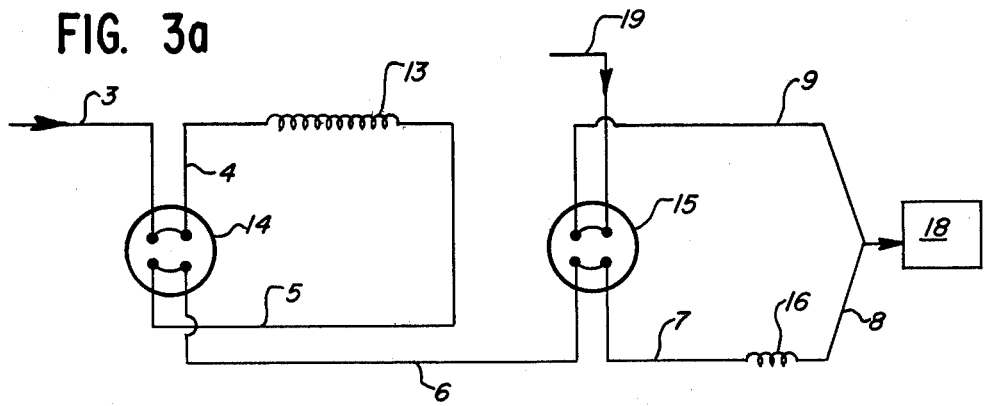
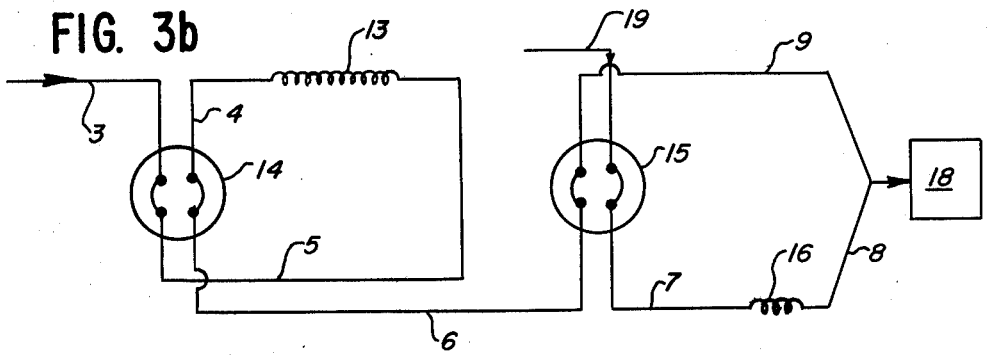
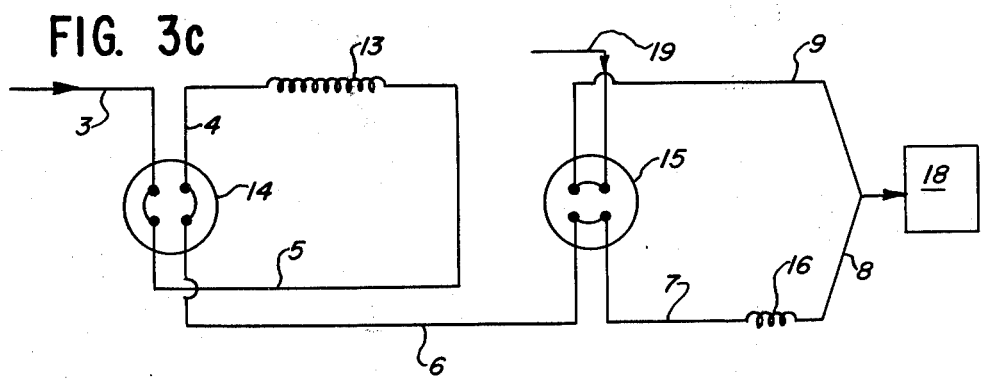

APPARATUS AND METHOD FOR ANALYZING THE HYDROCARBON TYPE COMPOSITION OF GASOLINE

BACKGROUND OF THE INVENTION

1. Field of the Invention

This invention relates to a method and an apparatus for analyzing the composition of gasoline-range petroleum products using a new copper on silica gel adsorption composition. More particularly, this invention relates to a copper on silica gel adsorption composition which can separate olefins in a composition comprised of olefins and saturates.

2. Description of the Prior Art

The present standard procedure for analyzing gasoline-range petroleum products is the fluorescent indicator adsorption (FIA) technique described in American Standard Test Measurement (ASTM) D-1319. This ASTM test covers the determination of saturates, olefins, and aromatics in petroleum fractions that distill below 600° F. (315° C.). The test involves a lengthy analysis requiring continuous operator attention and is subject to human variability and several interferences, such as aromatic olefins, some diolefins, and compounds containing sulfur, nitrogen, or oxygen being determined as aromatics. These limitations have inspired the development of numerous alternatives which have met with varying degrees of success. Of the various alternatives, most are gas chromatographic methods, all of which share a common weakness. This weakness is that the olefins, instead of being separated from the saturates and aromatics and measured directly, are permanently trapped. This means that the amount of olefins present in the sample cannot be measured directly and must be calculated by difference. Using such a system, false measurements are obtained, especially in samples containing only small amounts of olefins because one would be comparing a small difference between two relatively large values.

The present invention satisfactorily solves this separation and measurement problem by providing an apparatus and a method for directly measuring the hydrocarbon composition of a sample.

The general object of this invention is to provide a method and an apparatus for directly analyzing the composition of gasoline-range petroleum products. More specifically, the object of this invention is to use a copper on silica gel adsorption composition to separate olefins from a composition comprised of olefins and saturates.

A further object of this invention is to provide an improved method for analyzing gasoline compositions quickly and reliably.

Still further, an object of this invention is to provide a direct volume percent measurement and digital readout of the saturates, olefins, and aromatics in a gasoline sample.

Other objects of this invention will become apparent to one skilled in the art based upon the ensuing description.

SUMMARY OF THE INVENTION

Briefly, this invention provides a method and an apparatus for analyzing a gasoline composition, comprising saturates, olefins and aromatics, in a gasoline-range petroleum sample. Also disclosed is a new copper on silica gel adsorption composition which is capable of temporarily retaining olefins yet allowing saturates to pass through. The method comprises passing a gasoline sample along with a carrier gas through an absorption column whereby the saturates and olefins pass through while the aromatics are retarded. This is the first step in isolating each individual component of the sample so that the saturates, olefins and aromatics can be separately detected and directly measured. The effluent, comprised of saturates and olefins, which passed through the absorption column is then directed through a copper on silica gel column wherein the olefins are temporarily retained. This allows only the saturates to pass into a detector where they are measured. After all the saturates are withdrawn from the system, the aromatics are backflushed from the absorption column by additional carrier gas and are routed directly to the detector for measurement. This backflushing occurs prior to the time required for the first trace of aromatics to work its way completely through the length of the absorption column. The backflushing is carried out by reversing the flow of the carrier gas which initially passed through the absorption column. It should be pointed out that the aromatics bypass the copper on silica gel column on their way to the detector so as not to mix with the entrained olefins. After all the aromatics have been removed from the system, the copper on silica gel column is elevated in temperature until the olefins are released. Again, a stream of carrier gas is used to convey the olefins to the detector for measurement. The detector, which is preferably a flame ionization detector, is capable of measuring the amount of each component of the hydrocarbon composition. After the detector has measured the various components, the measured values are converted to useful percentages. The percentage value of the various components corresponds to the numerical numbers furnished by the Fluorescent Indicator Adsorption (F.I.A.) technique.

The apparatus for analyzing gasoline compositions according to the above described method comprises a heated enclosure which houses an absorption column, a multi-directional backflush valve and a multi-directional bypass valve. A sample cup and injector are situated upstream of this heated enclosure and provide a means for inserting a few microliters of the sample, into a compatible carrier gas, such as nitrogen. Downstream of the heated enclosure is a temperature controllable aluminum block containing a copper on silica gel composition which has the ability to temporarily retain olefins while allowing saturates to pass through. A detector is situated downstream of both the absorption column and the copper on silica gel composition and is used to measure the amount of saturates, olefins and aromatics in the sample. All of the above equipment is connected by conduits in such a fashion that one can separate the sample into individual components and route these components into the detector. The apparatus includes regulating means for switching the passages within each valve so as to alter the direction of the sample and control means for adjusting the temperature of both the copper on silica gel composition and the heated enclosure. By using such an apparatus, one is able to measure directly the saturates, olefins and aromatics contained in a sample of gasoline. This new method of analysis avoids the current problem associated with other gas chromatograph methods, that being the determination of olefins by difference.

In addition, this new inventive method can provide a reliable analysis in less than 30 minutes whereas the current F.I.A. technique takes several hours.

BRIEF DESCRIPTION OF THE DRAWINGS

FIG. 3a, 3b and 3c illustrate the three flow paths which are sequentially followed to separate out and measure the amounts of saturates, olefins and aromatics in a gasoline sample.

DETAILED DESCRIPTION OF THE INVENTION

Figure 1:
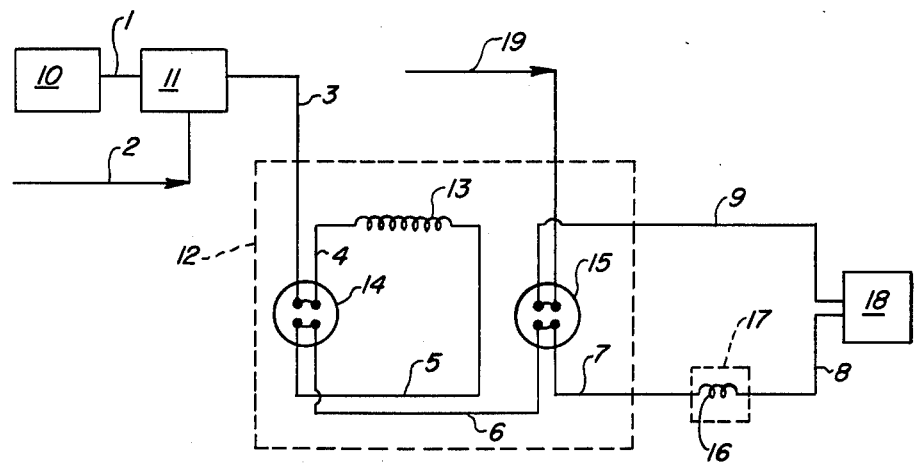
FIG. 1 shows a schematic of the apparatus used to measure directly the amounts of saturates, olefins and aromatics in a gasoline sample.

Referring now to FIG. 1 of the drawings, there is depicted a representative embodiment of a schematic of the apparatus used to directly measure the amount of saturates, olefins and aromatics in a gasoline sample.

As used throughout this application, the word olefin refers to a class of unsaturated aliphatic hydrocarbons containing 5-12 carbon atoms such as 2 methyl-2-butene, 1-hexene, 1,3-heptadiene and 1,5-heptadiene.

By this method, a liquid sample of gasoline is inserted into sample cup 10. A small portion of this sample, for example, a couple of microliters, preferably one to two microliters, is conveyed through conduit 1 to sample injector 11. The sample in sample injector 11 is then contacted with a carrier gas and is vaporized. The carrier gas which facilitates the transport of the sample through the system enters through line 2. The carrier gas must be chemically compatible and non-reactive with the sample as well as with the packed columns employed in the system. Nitrogen is the preferred carrier gas because it satisfies the above criteria. Another suitable carrier gas is helium. The sample along with the carrier gas is conveyed via conduit 3 into heated enclosure 12 which houses an absorption column 13, a multi-directional backflush valve 14, and a multi-directional bypass valve 15. As the sample is first introduced into heated enclosure 12 it is directed through backflush valve 14 and to absorption column 13 via line 4. Absorption column 13 is designed to retard the movement of aromatics while allowing the saturates and olefins to pass through. Absorption column 13 is preferably a column of 35% N,N-Bis(2-cyanoethyl) formamide on Chromosorb P, hereinafter referred to as a CEF column. The "N,N" refers to substitution occurring on nitrogen atoms and "Bis" refers to the stereochemical description of the substitution. The Chromosorb P support material can be acid washed and treated with dimethyl chlorosilane. The CEF column packing material can be purchased from Applied Science Laboratories, Inc., State College, Pa. The CEF column is a common gas chromatography column having an internal diameter of about 0.25 centimeters and a length of about 370 centimeters. The length and diameter of the column can vary as long as the column is able to sufficiently retard the passage of the aromatics. The aromatics should be retarded long enough so that the saturates and olefins can be separated and measured individually.

Other alternatives for the CEF column are columns containing a packing of 1,2,3-tris(2-cyanoethoxy)propane on Chromosorb P or columns containing a packing of OV-275 on Chromosorb P. Other suitable support material can be substituted for the Chromosorb P.

Figure 2:
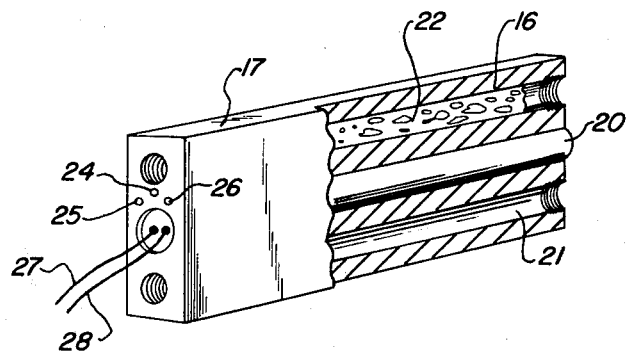
FIG. 2 illustrates a partial cross-sectional view of the aluminum block containing the copper on silica gel column.

While the flow of the aromatics is being retarded by absorption column 13, the saturates and olefins are passed through lines 5, 6 and 7 to copper on silica gel column 16. Copper on silica gel column 16 is contained in aluminum block 17 which is temperature controlled. An enlarged view of aluminum block 17 is shown in FIG. 2. Aluminum block 17 houses a cartridge heater 20, a cooling water passageway 21 and copper on silica gel column 16. Copper on silica gel column 16 is a cylindrical gas adsorption column comprising a chamber containing a packed material 22. Packing 22 is comprised of from about 65-90 weight percent of a solid granular silica gel material coated with about 10-35 weight percent of a cupric salt. The preferred cupric salt is cupric ammonia sulfate, $Cu(NH_3)_4SO_4$. The cupric salt is coated and/or impregnated on the silica gel material by commonly known techniques. For good results, packing 22 should have a pore diameter of at least 100 Å, preferably 130-150 Å, and most preferably 140 Å. The amount of copper adsorbed onto packing 22 should be about 3-10%. Like absorption column 13, the copper on silica gel adsorption column 16 can be of any desirable internal diameter and length as long as it can separate the olefins from the saturates. An adequate size is a copper on silica gel column having an internal diameter of approximately 0.50-1.50 centimeters and a length of about 5-15 centimeters.

While this invention is primarily directed to the analysis of the amount of olefins in hydrocarbon compositions, it is within the scope of this invention to use a copper on silica gel composition to separate olefins from a mixture of olefins and saturates. In such a use, the olefin and saturate mixture is passed through a copper on silica gel composition whereby the olefins are adsorbed while the saturates pass through. The copper on silica gel composition can then be heated thereby releasing adsorbed material. Such a separation can be carried out in a batch process or in a continuous process.

Referring again to FIG. 2, aluminum block 17 houses a thermocouple well 24 and sensor wells 25 and 26. A thermocouple and sensors are situated in wells 24, 25 and 26 respectively and are used to monitor and sense the temperature changes occurring within copper on silica gel column 16. This is necessary because copper on silica gel column 16 must be cycled in temperature in order that a separation between saturates and olefins is effected. The rapid temperature changes occur from the heat input supplied by cartridge heater 20 and the cooling provided by cooling water passageway 21. Other cooling means can be substituted for the cooling water if desired. Cartridge heater 20 is connected to an electrical source by leads 27 and 28. The heating and cooling cycles can be controlled by an automatic control system, such as a computer. In operation, the copper on silica gel column 16 is maintained at about 200°-225° C. when the saturates and olefins pass into contact with it. When the time comes to release the olefins from the copper on silica gel column 16, the temperature of column 16 is elevated to approximately 350°-400° C., preferably about 375° C. This higher temperature allows the olefins to be either desorbed or thermally decomposed and thereby become free of the packing 22 in column 16.

Referring again to FIG. 1, the saturates and olefins are directed through line 7 to copper on silica gel column 16 wherein the olefins are temporarily retained. This permits the saturates alone, with the aid of the carrier gas, to pass via line 8 directly to detector 18 for measurement. Detector 18 can be a flame ionization detector which measures the amount of each separate component which is fed into it. It is advantageous to electrically connect detector 18 to a computer or other memory device so that the detected values can be mathematically calculated and stored for future use. Once the amount of saturates present in the hydrocarbon sample have been determined, backflush valve 14 and bypass value 15 are switched and the aromatics are backflushed from absorption column 13. Valves 14 and 15 are switched from the position depicted in FIG. 3(*a*) to that shown in FIG. 3(*b*). In this configuration, the aromatics pass directly through line 9 to detector 18 and are measured. The flow of the aromatics is facilitated by additional carrier gas conveyed through line 3. Also, a steady stream of carrier gas is introduced via line 19 to insure that no aromatics get sidetracked in line 8. An adequate flow rate for such a system is from about 50–150 cubic centimeters/minute, preferably 100–130 cubic centimeters/minute. Once all the aromatics have been flushed from the system by the carrier gas, bypass valve 15 is again switched, see FIG. 3(*c*), to its original position and copper on silica gel column 16 is heated up to a sufficient temperature so that the olefins are released. At such a temperature the olefins are released from copper on silica gel column 16 and are swept through line 8 to detector 18 for measurement.

When first starting up the above described apparatus, it is advantageous to allow the instrument to be warmed up. Heated enclosure 12 should be heated to about 50° C. and copper on silica gel column 16 should be raised to about 200°–225° C. If a fresh copper on silica gel column 16 is used, it must be thoroughly purged with carrier gas at about room temperature. Then, after a warm up period, it is necessary to condition copper on silica gel column 16 by exposing it to several sample runs of olefinic material. The purging is necessary to remove oxygen which is a poison to copper on silica gel column 16 at high temperatures. The conditioning presumably covers up extremely active sites on packing 22 which would not release olefins even at temperatures in the 350°–400° C. range.

Once the instrument is sufficiently warm, it must be calibrated by running a known standard sample through it and adjusting the measurement signal processor. The signal processor calculates and transforms the measured signals to corresponding values. Signal processors are commercially available and known in the prior art. The standard sample values can be adjusted to correspond to FIA values if desired. After calibration the instrument is ready for use.

Although the invention has been described in detail for the purposes of illustration, it is to be understood that such detail is solely for that purpose and that variations can be made therein by those skilled in the art without departing from the spirit and scope of the invention, except as it may be limited by the claims.

I claim:

1. A method for separating olefins from saturates in a composition comprised of a number of olefins having between 5 and 12 carbon atoms and saturates which comprises:
   (a) passing said composition into contact with a copper on silica gel composition whereby said olefins are adsorbed while said saturates pass through; and
   (b) thereafter heating said copper on silica gel composition to release said olefins.

2. The method of claim 1 wherein the copper on silica gel composition is maintained at about 200°–225° C. during step (a) and is heated to about 350°–400° C. during step (b).

3. A method for analyzing a gasoline sample comprising saturates, olefins and aromatics, which method comprises:
   (a) passing said sample through an absorption column whereby said aromatics are retarded while the effluent passes through;
   (b) passing said effluent from step (a) through a copper on silica gel column wherein said olefins are adsorbed and temporarily retained;
   (c) detecting the amount of said saturates present in said sample;
   (d) backflushing said aromatics from said absorption column;
   (e) detecting the amount of said aromatics present in said sample;
   (f) heating said copper on silica gel column to release said olefins; and
   (g) detecting the amount of olefins present in said sample.

4. The method of claim 3 wherein a carrier gas is used to facilitate transport of said sample through said columns.

5. The method of claim 4 wherein said carrier gas is nitrogen.

6. The method of claim 4 wherein said carrier gas is chemically compatible and nonreactive with said sample.

7. The method of claim 4 wherein said carrier gas is compatible and nonreactive with columns.

8. The method of claim 3 wherein said saturates, olefins and aromatics in said sample are detected with a flame ionization detector.

9. The method of claim 3 wherein the copper on silica gel column is maintained at a temperature of about 200°–225° C. during adsorption of olefins and at a temperature of approximately 350°–400° C. during release thereof.

10. A method for analyzing the saturates, olefins and aromatics content in a gasoline sample by utilizing a carrier gas to move said sample through valves and columns to a detector, which comprises:
    (a) passing said sample through an absorption column whereby said aromatics are retarded while said saturates and olefins pass through;
    (b) passing said saturates and olefins from step (a) through a copper on silica gel column wherein said olefins are temporarily retained while said saturates pass through;
    (c) detecting the amount of saturates present in said sample;
    (d) backflushing with carrier gas said aromatics from said absorption column directly to said detector;
    (e) detecting the amount of aromatics present in said sample;
    (f) heating said copper on silica gel column from about 200° C. to about 375° C. whereby said olefins are released from said column; and
    (g) detecting the amount of olefins present in said sample.

11. An apparatus for analyzing the compositions of various gasoline samples, which comprises:
    (a) a sample injector;

(b) an absorption column for retarding aromatics contained in said sample;

(c) a copper on silica gel adsorption column for separating olefins from saturates contained in said sample;

(d) a valve means for reversing the flow of said sample through said absorption column for retarding aromatics;

(e) a valve means for directing the flow of said sample around said copper on silica gel adsorption column;

(f) a means for detecting the amount of aromatics, olefins and saturates contained in said sample;

(g) conduits adjoining said aforementioned columns, valves and detecting means;

(h) temperature control means for controlling the temperature of said copper on silica gel adsorption column; and (i) a means for controlling said valve means to control the direction of flow of said sample to said detector.

12. An apparatus for analyzing the compositions of various gasoline samples, which comprises:

(a) a heated enclosure housing an absorption column for retarding the flow of aromatics, a multidirectional backflush valve and a multi-directional bypass valve;

(b) a sample injector positioned upstream of said heated enclosure;

(c) a temperature controllable aluminum block containing a copper on silica gel column for temporarily retaining olefins, said block situated downstream of said heated enclosure;

(d) a detector positioned downstream from said columns;

(e) conduits connecting said backflush valve to said sample injector and to both ends of said absorption column, and to said bypass valve;

(f) conduits directly connecting said bypass valve to said copper on silica gel column and to said detector;

(g) a conduit connecting said copper on silica gel column to said detector;

(h) a carrier gas inlet line attached to said bypass valve;

(i) means for injecting a sample along with a carrier gas into said injector;

(j) means for regulating said valves to alter the direction of said sample through said columns;

(k) means for controlling the temperature of said copper on silica gel column.

* * * * *